United States Patent [19]

Jarreau et al.

[11] Patent Number: 4,716,171
[45] Date of Patent: Dec. 29, 1987

[54] ANTIARRHYTHMIC QUINIDINE DERIVATIVES

[75] Inventors: Francois-Xavier Jarreau, Versailles; Jean-Jacques Koenig, Vernou la Celle s/Seine, both of France

[73] Assignee: Etablissements Nativelle S.A., France

[21] Appl. No.: 597,219

[22] Filed: Apr. 9, 1984

Related U.S. Application Data

[63] Continuation of Ser. No. 380,316, May 20, 1982, abandoned.

[30] Foreign Application Priority Data

May 20, 1981 [FR] France ................. 81 10024

[51] Int. Cl.[4] ............... A61K 31/49; C07D 453/04
[52] U.S. Cl. .................. 514/305; 546/134; 546/136
[58] Field of Search ............. 546/134, 136; 424/259; 514/305

[56] References Cited

U.S. PATENT DOCUMENTS

4,338,320 7/1982 Rosenberg et al. ............. 424/259

OTHER PUBLICATIONS

Beermann, B., et al., *Acta Chem. Scand.* 1976, B30, p. 465.
Palmer, K., et al., *Biochem. Pharmacol.* 1969, 18, 1845-1880.
Carroll, F., et al., *J. Med. Chem.*, 17, 985-987 (1974).
Liddle, C., et al., *Xenobiotica*, 1981, 11(2), 81-87.
Merck Index, Eighth Edition, p. 903.
Low, L., et al., in *Burger's Medical Chemistry*, 4th ed., Wiley Interscience, New York, 1980, vol. 1, pp. 136-145.
Carroll, F., et al., *Tett. Lett.* No. 21, 1757 (1976).
House, H., *Modern Synthetic Reactions*, 2nd ed., Benjamin/Cummings, Menlo Park, CA, 1972, p. 13.
House, H., *Modern Synthetic Reactions*, 2nd ed., Benjamin/Cummings, Menlo Park, CA, 1972, p. 9.
*Chemical Abstracts*, 95:90722a (1981) [Liddle, C., et al., *Xenobiotica* 1981, 11(2), 81-7].
House, H., *Modern Synthetic Reactions*, 2nd ed., Benjamin/Cummings, Menlo Park, CA, 1972, p. 10.

*Primary Examiner*—Richard A. Schwartz
*Attorney, Agent, or Firm*—Sughrue, Mion, Zinn, Macpeak & Seas

[57] ABSTRACT

Quinidine derivatives of general formula (I):

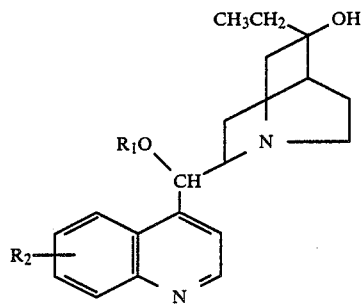

wherein $R_1$ represents a hydrogen atom, an alkyl group, or an acyl group, and $R_2$ represents a hydrogen atom, a hydroxy group, an alkoxy group, an acyloxy group or an aroyloxy group, as well as the acid addition salts thereof, useful in therapy, particularly, for the treatment of cardiac arrhythmia.

13 Claims, No Drawings

ANTIARRHYTHMIC QUINIDINE DERIVATIVES

This application is a continuation of application Ser. No. 380,316, filed May 20, 1982, now abandoned.

FIELD OF THE INVENTION

The present invention relates to new quinidine derivatives, a process for their preparation and their use in therapy.

BACKGROUND OF THE INVENTION

It is known that quinidine possesses therapeutic properties which allow its use for the treatment of various cardiac, ventricular or supra-ventricular arrhythmias. The administration of quinidine may, however, be accompanied by certain disadvantages such as, for example, digestive problems, and it has often appeared desirable to be able to use medication with the basic properties of quinidine, possibly possessing greater efficacity, but without certain troublesome side effects.

Certain compounds are known which are derived from quinidine and are obtained by esterification by means of an appropriate agent, such as the quinidine alginate described in French Pat. No. 2,115,199 or a quinidine polysaccharide sulfate as described in French Pat. No. 2,013,170 or even the dihydroquinidine galacturonate as described in U.S. Pat. No. 3,479,359. However, if such derivatives do occasionally provide an attenuation of certain of the disadvantages of quinidine, they cannot improve on or modify the activity thereof, and their use does not always prove satisfactory.

SUMMARY OF THE INVENTION

An object of the present invention is new dihydroquinidine derivatives having therapeutic activities close to those of quinidine, and more particularly new dihydroquinidine derivatives which are hydroxylated at the 3-position, which may be used in therapy and are likely to be better adapted to the treatment of cardiac arrhythmias, as well as a process for the preparation of these derivatives.

The new compounds according to the present invention are 3-hydroxy 10,11-dihydroquinidine, and its derivatives, represented by the general formula (I):

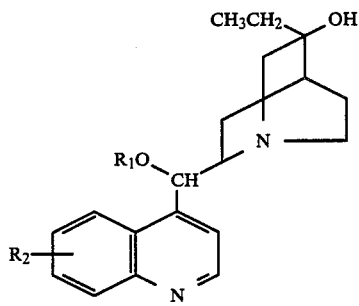

wherein $R_1$ represents a hydrogen atom, an alkyl group or an acyl group, and $R_2$ represents a hydrogen atom, a hydroxy group, an alkoxy group, an acyloxy group or an aroyloxy group.

DETAILED DESCRIPTION OF THE INVENTION

In the general formula (I) above, $R_1$ can in particular represent a hydrogen atom or an alkyl group, preferably a lower alkyl group with 1 to 4 carbon atoms such as methyl, ethyl, isopropyl, etc., or an acyl group such as formyl, acetyl, butyroyl, etc. $R_2$ can represent a hydrogen atom, a hydroxy group, an alkoxy group, and preferably a lower alkoxy group with 1 to 4 carbon atoms, such as methoxy, ethoxy, isopropoxy, n-propoxy, etc., an acyloxy group and preferably an acetoxy or formyloxy group, or even an aroyloxy group such as a benzoyloxy group. The substituent represented by $R_2$ can be at various positions of the quinolinyl nucleus, and preferably occupies the 6'-position.

The invention preferably relates to compounds of the general formula (I), wherein $R_1$ is a hydrogen atom or an acetyl group, and $R_2$ is a hydrogen atom or a lower alkoxy, hydroxy or acetoxy group at the 6'-position.

The invention relates in particular to the isomers of the derivatives of formula (I) and in particular to 3S-hydroxydihydroquinidine, 3R-hydroxydihydroquinidine, and a mixture of epimers at the 3-position, whose existence is due to the presence of an asymmetrical carbon at the 3-position. These isomers are obtained from 3S-hydroxyquinidine, 3R-hydroxyquinidine and from a mixture of epimers at the 3-position, respectively, as described in greater detail below.

In accordance with the present invention the quinidine derivatives of general formula (I) above can be prepared from derivatives of general formula (II):

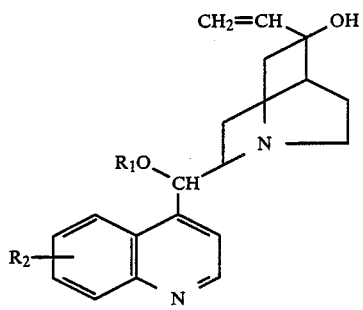

wherein $R_1$ is a hydrogen atom or an acetyl group and $R_2$ is a hydrogen atom or a methoxy group, by carrying out a hydrogenation reaction, followed as necessary by acylation or demethylation.

The acylation reaction carried out as necessary after the hydrogenation reaction yields the products of formula (I) where $R_1$ is an acyl group from the derivatives of formula (II) where the corresponding $R_1$ group is a hydrogen atom. Likewise, alkylation can be carried out in order to obtain products where $R_1$ is an alkyl group. The demethylation reaction is carried out as necessary to transform the methoxy group represented by $R_2$ in formula (II) into a hydroxy group. By then carrying out alkylation or acylation, the products of formula (I) are obtained where $R_2$ is an alkoxy or acyloxy (or aroyloxy) group, respectively. All these reactions can be carried out using conventional techniques.

The 3-hydroxy quinidine derivatives of formula (II) are known compounds which can be prepared using conventional methods. For example, the 3-hydroxyquinidine represented by the formula (II), wherein $R_1$ is a hydrogen atom and $R_2$ is a methoxy group, is a known quinidine metabolite which can be prepared by the method of F. I. Carroll et al., *Tetrahedron Letters*, No. 21, p. 1757–1760 (1976). This method can also be used for the preparation of other compounds of general formula (II).

The hydrogenation reaction yielding the 3-hydroxy 10,11-dihydroquinidine derivatives from the compounds of general formula (II) can be carried out using conventional techniques. The catalytic hydrogenation reaction can be carried out by means of a noble metal-based catalyst such as platinum, palladium or rhodium, or a Raney nickel catalyst. The palladium or rhodium used as a catalyst is deposited on a support such as carbon or alumina.

For example, catalytic hydrogenation can be carried out by dissolving the compound of formula (II) in an appropriate organic solvent under a hydrogen atmosphere in the presence of a palladium/carbon catalyst.

An alcohol such as methanol, ethanol or isopropanol can, for example, be used as the solvent. The reaction can be carried out at ambient temperature under normal pressure.

The invention also relates to salts of the quinidine derivatives represented by the general formula (I) above, and, in particular, to the pharmaceutically acceptable salts, obtained by reacting a mineral or organic acid on the quinidine derivative as base. These salts can be obtained by methods conventional in the art, by reacting the quinidine derivative and the acid, in largely stoichiometric proportions, in a compatible solvent. The acid can, for example, be hydrochloric acid, lactic acid, oxalic acid, phosphoric acid, hydrobromic acid, formic acid, sulfuric acid, tartaric acid, maleic acid, etc.

It is interesting to observe that 3-hydroxyguinidine, a known metabolite of quinidine, possesses certain pharmacological properties comparable to those of quinidine, which have not, however, justified more in-depth clinical studies, and although it is known, this compound has not been used in therapy. It may appear surprising under these circumstances that 3-hydroxy-10,11-dihydroquinidine, a corresponding compound whose double bond at the 10-11 position has been reduced, possesses pharmacological activity not only comparable to that of quinidine, but even greater for certain properties.

The pharmacological properties and the therapeutic applications of the 3-hydroxy-10,11-dihydroquinidine derivatives of the present invention, as well as non-limitative examples of the preparation of preferred compounds, are described below in greater detail.

EXAMPLE 1

3S-Hydroxy-10,11-dihydroquinidine 0.7 g of 3S-hydroxyquinidine was dissolved in 10 ml of methanol. 65 mg of palladium-on-carbon catalyst were added and the reactive medium was placed under a hydrogen atmosphere for 10 minutes.

When the reaction was terminated, the catalyst was filtered off. The filtrate was evaporated until dry and then the residue was recrystallized from ethyl acetate.

In this manner 3S-hydroxy-10,11-dihydroquinidine with a yield of 90% was obtained.

Melting Point F=210° C. (ethyl acetate).

IR Spectrum (Nujol) $v=3600$ to 2200 (peaks at 3510 and 3320), 1620, 1590, 1565 and 1510 cm$^{-1}$.

NMR Spectrum (CD$_3$OD) $\delta=0.95$ (t, 3H); 1.1 to 3.9 (12H); 3.9 (s, 3H); 5.6 (d, 1H); 7.2 to 8.0 and 8.6 (5H) ppm.

EXAMPLE 2

3R-Hydroxy-10,11-dihydroquinidine

The process of Example 1 was repeated replacing the 3S-hydroxyquinidine with 3R-hydroxyquinidine. In this manner 3R-hydroxy 10,11-dihydroquinidine was obtained with a yield of greater than 90%.

Melting Point F=189° C. (ethyl acetate).

IR Spectrum (Nujol) $v=3600$ to 2400 (peaks at 3440, 3100 and 2740), 1620, 1585, 1570 and 1510 cm$^{-1}$.

NMR Spectrum (CDCl$_3$) $\delta=0.9$ (t, 3H); 1.2 to 3.5 (13H); 3.8 (s, 3H); 5.0 (1H, mobile); 5.6 (s, 1H); 7.0 to 8.4 (5H) ppm.

EXAMPLE 3

3S-Hydroxy O-acetyl-10,11-dihydroquinidine 0.6 g of 3S-hydroxy-10,11-dihydroquinidine obtained as indicated in Example 1 was dissolved in 10 ml of methylene chloride and 0.3 g of acetic anhydride was poured dropwise into this solution. The product formed was collected and purified using conventional techniques.

In this manner 3S-hydroxy-O-acetyl-10,11-dihydro quinidine was obtained with a yield of 95%.

Melting Point F=130°-132° C. (ethyl acetate).

IR Spectrum (Nujol) $v=3500-2500$ (maximum at 3060), 1735, 1615, 1585, 1565, 1505 cm$^{-1}$.

The evaluations carried out on the 3-hydroxydihydroquinidine derivatives have brought out interesting pharmacological properties showing that the derivatives of the present invention can be used in veterinary or human therapy.

Toxicological Properties

The LD$_{50}$ value was measured in accordance with the Lichfield and Wilcoxon method (*J. Pharmacol.* 96, 99–113 (1949)) on mice and rats (10 animals: 5 males and 5 females per dose).

The values noted for LD$_{50}$ are on the order of 90 to 150 mg/kg for intravenous injection (IV), 200 to 400 mg/kg for intraperitoneal injection (IP) and 850 to 1100 mg/kg for administration orally in mice. The LD$_{50}$ value for rats is on the order of 600 to 700 mg/kg for administration orally.

For example, the results obtained with 3S-hydroxy-10,11-dihydroquinidine in the form of the hydrochloride salt are shown in Table 1 below.

TABLE 1

| | Mice | | | | | | Rats | | |
|---|---|---|---|---|---|---|---|---|---|
| | | | | Sex | | | | | |
| | Male | | | Female | | | Male | Female | |
| | | | | Administration | | | | | |
| | IV | IP | Oral | IV | IP | Oral | Oral | Oral | |
| LD$_{50}$ | 120 | 280 | 975 | 105 | 180 | 900 | 640 | 640 | mg/kg |

By way of comparison, the average values for LD$_{50}$ for quinidine by intraperitoneal administration in mice (male and female) are 225–235 mg/kg. These values show that the toxicity of the quinidine derivatives of the present invention is not increased in relation to quinidine, but to the contrary seems attenuated.

Pharmacological Properties

The hemodynamic effects caused by cumulative doses of 3S-hydroxy-10,11-dihydroquinidine in dogs were measured. The results obtained are given in Table 2 below.

The parameters were recorded by means of:

catheters connected to pressure sensors (arterial pressure, left ventricular pressure and its first dp/dt derivative);
electromagnetic flowmeter on the aorta (aortic flow);
electrocardiograph;
strain gauge placed on the left ventricular myocardium (myocardiac contraction force).

The derivatives were injected intravenously, one dose every 30 minutes approximately and their effects were measured 20 minutes after the end of the injection (length of time of the injection: 2 minutes).

TABLE 2

|  | Initial Values | Cumulative Dose (mg/Kg I.V.) | | | | |
| --- | --- | --- | --- | --- | --- | --- |
|  |  | 0.5 | +0.5 | +4 | +5 | +10 |
| Systolic Arterial Pressure (mmHg) | 130 ± 6 | −3 ± 3 | −11 ± 4 | −20 ± 5 | −23 ± 7 | −36 ± 13 |
| Cardiac Frequency (beats/min.) | 140 ± 11 | 0 ± 0 | −2 ± 6 | −5 ± 2 | −3 ± 16 | −15 ± 13 |
| Cardiac Flow (ml/min.) | 2800 ± 246 | 0 ± 0 | −50 ± 50 | −90 ± 143 | −316 ± 412 | −775 ± 498 |
| Force of Contractions of the Myocardium (g) | 33 ± 3 | −1 ± 1 | −3 ± 3 | 0 ± 1 | 2 ± 1 | 8 ± 1 |
| Total Peripheral Resistance | 3119 ± 415 | −111 ± 111 | −382 ± 180 | −457 ± 277 | −376 ± 227 | −91 ± 283 |

The results summarized in this table, expressed in variation in relation to the initial value, 20 minutes after injection, show that the derivative studied in dogs causes the following changes:
- systolic arterial pressure diminishes progressively with the dose, the effects only becoming considerable for a cumulative dose greater than 10 mg/kg;
- cardiac frequency is not significantly modified before a cumulative dose of 20 mg/kg is reached;
- likewise, cardiac flow undergoes no significant change before a cumulative dose of 20 mg/kg is reached;
- no change of the myocardiac contraction force was observed.

From this it can be concluded that the cardiovascular tolerance in dogs is satisfactory, since the effects are limited to a moderate decrease in arterial pressure, without change in the myocardiac contractile force and without a considerable decrease in the cardiac flow, for cumulative doses of less than 20 mg/kg.

Table 3 below summarizes the electrophysiological data relative to the administration of 3S-hydroxydihydroquinidine, by comparison with quinidine.

The study was carried out on a dog anesthetized with pentobarbital, with a closed thorax, by means of bipolar catheter-electrodes introduced into the cardiac cavities by transcutaneous venous and arterial tracts.

In this manner and by means of a programmable stimulator, sinusal automaticity, intracardiac conduction times, and the effective and functional cardiac refractory periods can be measured.

TABLE 3

|  | DOSES (mg/kg) | | |
| --- | --- | --- | --- |
|  | 1 | 5 | 10 |
| Cardiac Cycle |  |  |  |
| Invention | +4.5% | +5.1% | +14.% |
| Quinidine | +2.7 | +5.1 | +9.2 |
| SH* |  |  |  |
| Invention | +1.7 | +3.8 | +15 |
| Quinidine | +3.5 | +7.2 | +10.5 |

TABLE 3-continued

|  | DOSES (mg/kg) | | |
| --- | --- | --- | --- |
|  | 1 | 5 | 10 |
| HV* |  |  |  |
| Invention | +10.8 | +20.9 | +32.8 |
| Quinidine | 0 | +8.7 | +17.7 |
| QRS* |  |  |  |
| Invention | +14.4 | +14.4 | +22 |
| Quinidine | 0 | 0 | 0 |
| PREA* |  |  |  |
| Invention | +8 | +16 | +23.7 |
| Quinidine | +2 | +3.5 | +14.4 |
| PRFN* |  |  |  |
| Invention | 0 | +5.5 | +12.6 |
| Quinidine | +3 | +5 | +9 |
| PREV* |  |  |  |
| Invention | −1.5 | +2.8 | +6.5 |
| Quinidine | +3.3 | +6.5 | +8.5 |
| QT$_c$* |  |  |  |
| Invention | +2.8 | +7 | +6 |
| Quinidine | +1.8 | 0 | +1.5 |

*SH: Auriculo-Hissian conduction
HV: Hiss-Purkinje conduction
QRS: Intra-ventricular conduction
PREA: Effective auricular refractory period
PRFN: Functional nodal refractory period
PREV: Effective ventricular refractory period
QT$_c$: Corrected repolarization time.

The results shown in Table 3 expressing the percentages of variation of the different parameters show that the compound of the present invention,
- slows cardiac frequency like quinidine;
- slightly changes conduction between the auricles and the trunk of the His fasciculus, whereas it exerts effects greater than those of quinidine on conduction in the His-Purkinje system (similar effects are observed with respect to intraventricular conduction);
- exerts, for the cardiac refractory periods, effects equivalent to those of quinidine at the ventricular and nodal stage, and greater than those of quinidine at the level of the auricles.

Antiarrhythmic activity in mice was observed by means of the Lawson test, using the method described by J. W. Lawson, *J. Pharmacol. Exp. Therp.*, 160, 22–31 (1968) and Cr. Narcisse et al. *Ann. Pharma. Fr.*, 37, 325–330 (1979), in rats by the test with aconitine of S. Witchitz et al. *Coeur Med. Int.*, X(2), 281–286 (1971), and in dogs by the Harris test described in *Circulation*, 1, 1318 (1950). 3S-hydroxy-10,11-dihydroquinidine was used for each of these three tests.

The results are set forth in Table 4 below. In the three cases, the activity has been compared to that of quinidine as a reference product.

TABLE 4

| TEST | ANIMAL SPECIES | METHOD OF ADMINISTRATION | DOSE | INVENTION | | QUINIDINE | |
| --- | --- | --- | --- | --- | --- | --- | --- |
| Lawson | Mice | I.P. | — | ED 50: | 72.5  6.94 mg/kg | 54 | 6.58 mg/kg |

TABLE 4-continued

| TEST | ANIMAL SPECIES | METHOD OF ADMINISTRATION | DOSE | | INVENTION | | | QUINIDINE | |
|---|---|---|---|---|---|---|---|---|---|
| Aconitine | Rats | I.V. | 10 mg/kg | | Appearance Time | | | Appearance Time | |
| | | | | Disorder | min. | % | | % | min. |
| | | | | ESV (98)* | 208 | +112 | | +53 | 150 |
| | | | | TV (112) | 253 | +125 | | +52 | 171 |
| | | | | FV (228) | 504 | +121 | | +107 | 474 |
| Harris | Dogs | I.V. | | Time | % Protection | | | Time | |
| | | | | Observed | Exp. 1 | Exp. 2 | Average | Observed | % Protection |
| | | | 6 mg/kg | 1 h. | 65 | 39 | 52 | 1 h. | 21 |
| | | | +10 mg/kg | 1 h. | 72 | 42 | 57 | +5 mg 1 h. | 55 |
| | | | | 2 h. | 97 | 41 | 69 | 2 h. | 52 |

*Control appearance time

The Lawson test enables the study of the cardiac antifibrillatory power of the derivatives of the present invention. It shows that the antifibrillatory efficacity of the derivative of the present invention is comparable to that of quinidine. The efficacity dose 50 ($ED_{50}$) indicated in Table 4 is the dose which protects half of the mice against anoxic ventricular fibrillation.

The test with aconitine shows that the derivative of the present invention exerts a protective effect against arrhythmia which is greater than that of quinidine, since more than quinidine, it prolongs the appearance time of ventricular extrasystoles (ESV) of ventricular tachycardium (TC) and of ventricular fibrillation (FV).

The results of the Harris test demonstrate that the decrease in ventricular arrhythmia, at a dose of 6 mg/kg, is greater with the compound of the present invention than with quinidine. It can be noted, moreover, that the efficacity of the products is comparable for higher doses.

These results show that the quinidine derivatives of the present invention possess antiarrhythmic properties similar to those of quinidine, on the qualitative level. On the quantitative level, it can in particular be noted that 3S-hydroxy-10,11-dihydroquinidine is considerably more active than quinidine in the test with aconitine.

Moreover, it must be observed that the electrophysiological activity at the His-ventricle conduction level constitutes an advantage in relation to quinidine.

These properties show that the quinidine derivatives of the present invention can be used in human and veterinarian therapy for the same applications as quinidine, and in particular in the treatment of various forms of cardiac arrhythmias, both supra-ventricular and ventricular.

The quinidine derivatives of general formula (I) and their pharmaceutically acceptable salts can be administered in common forms, the active constituent being diluted in an appropriately selected pharmaceutically acceptable carrier, for example, in the form of tablets, capsules, lozenges, suppositories, injectable solutions or syrups.

By way of example, the tablets can be prepared by mixing the quinidine derivative of general formula (I) or one of its salts, with one or more solid diluents, such as lactose, mannitol, starch, polyvinylpyrrolidone, magnesium stearate, talc, etc. Where necessary, the tablets may comprise several layers superposed around a nucleus, in accordance with conventional techniques, to ensure progressive availability or a delayed effect of the active constituent. The coating may, for example, be composed of one or more layers of polyvinyl acetate, carboxymethylcellulose or cellulose acetate phthalate.

The derivative of the invention may also be administered in the form of a syrup or drinkable solution obtained by dissolving the derivative of formula (I) or one of its pharmaceutically acceptable salts, in water or glycerol, for example, and adding, as necessary, a conventional additive such as a sweetener and an antioxidant.

Injectable solutions can be prepared using well-known techniques and are composed, for example, of a solution containing a derivative of formula (I) or one of its pharmaceutically acceptable salts, dissolved in bidistilled water, a hydroalcoholic solution, propyleneglycol, etc., or a mixture of these solvents. As necessary, an appropriate additive such as a preservative may be added.

The dosage may vary in accordance with the type of condition treated and the subject being treated. Doses administered daily are generally comparable to those of treatments with quinidine, but can be adjusted by the practitioner according to the circumstances.

While the invention has been described in detail and with reference to specific embodiments thereof, it will be apparent to one skilled in the art that various changes and modifications can be made therein without departing from the spirit and scope thereof.

What is claimed is:

1. A quinidine derivative of formula (I):

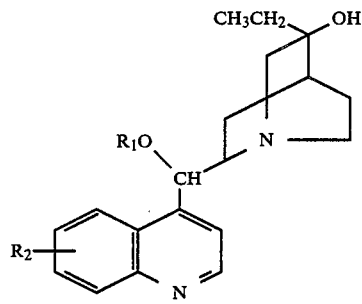

wherein $R_1$ represents a hydrogen atom, an alkyl group with 1 to 4 carbon atoms or an acyl group with 1 to 4 carbon atoms, and $R_2$ represents a hydrogen atom, a hydroxy group, an alkoxy group with 1 to 4 carbon atoms, an acetoxy group, a formyloxy group or a benzoyloxy group or an acid addition salt thereof.

2. The derivative of claim 1, wherein $R_1$ is a hydrogen atom, a lower alkyl group with 1 to 4 carbon atoms, or an acetyl group, and $R_2$ is a hydrogen atom, a hydroxy group, a lower alkoxy group with 1 to 4 carbon atoms, or an acetoxy group.

3. The derivative of claim 1, wherein R₁ is a hydrogen atom, a methyl group or an acetyl group, and R₂ is a hydrogen atom, a hydroxy group, an acetoxy group, a methoxy group, an ethoxy group or a propoxy group, at the 6'-position.

4. The derivative of claim 1, 2 or 3, selected from the group consisting of 3S-hydroxy-10,11-dihydroquinidine, 3R-hydroxy-10,11-dihydroquinidine, 3R-hydroxy-O-acetyl-10,11-dihydroquinidine, and 3S-hydroxy-O-acetyl-10,11-dihydroquinidine.

5. A pharmaceutical composition for the treatment of cardiac arrhythmias comprising a therapeutically effective amount of a derivative of claim 1, 2 or 3, or a pharmaceutically acceptable salt thereof and a pharmaceutically acceptable carrier or diluent.

6. A pharmaceutical composition for the treatment of cardiac arrhythmias comprising a therapeutically effective amount of a derivative of claim 4, or a pharmaceutically acceptable salt thereof and a pharmaceutically acceptable carrier or diluent.

7. A substantially pure preparation of a quinidine derivative of formula (I):

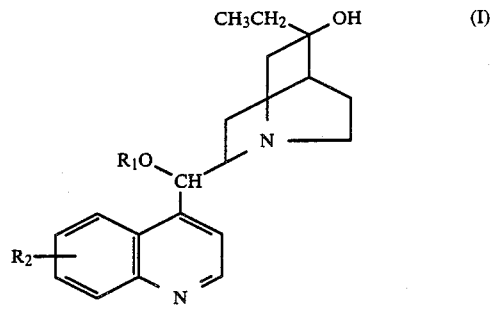

wherein R₁ represents a hydrogen atom, an alkyl group with 1 to 4 carbon atoms or an acyl group with 1 to 4 carbon atoms, and R₂ represents a hydrogen atom, a hydroxy group, an alkoxy group with 1 to 4 carbon atoms, an acetoxy group, a formyloxy group or a benzoyloxy group or an acid addition salt thereof.

8. The preparation of claim 7, wherein in the formula (I), R₁ is a hydrogen atom, a lower alkyl group with 1 to 4 carbon atoms, or an acetyl group, and R₂ is a hydrogen atom, a hydroxy group, a lower alkoxy group with 1 to 4 carbon atoms, or an acetoxy group.

9. The preparation of claim 7, wherein in the formula (I), R₁ is a hydrogen atom, a methyl group or an acetyl group, and R₂ is a hydrogen atom, a hydroxy group, an acetoxy group, a methoxy group, an ethoxy group or a propoxy group, at the 6'-position.

10. The preparation of claim 7, 8, or 9, wherein the compound of the formula (I) is selected from the group consisting of 3S-hydroxy-10,11-dihydroquinidine, 3R-hydroxy-10,11-dihydroquinidine, 3R-hydroxy-O-acetyl-10,11-dihydroquinidine, and 3S-hydroxy-O-acetyl-10,11-dihydroquinidine.

11. 3S-hydroxy-10,11-dihydroquinidine.

12. A pharmaceutical composition for the treatment of cardiac arrhythmias comprising a therapeutically effective amount of 3S-hydroxy-10,11-dihydroquinidine or a pharmaceutically acceptable salt thereof and a pharmaceutically acceptable carrier or diluent.

13. A method for the treatment of cardiac arrhythmias comprising administering to a subject afflicted with cardiac arrhythmia a therapeutically effective amount of 3S-hydroxy-10,11-dihydroquinidine or a pharmaceutically acceptable salt thereof.

* * * * *